US009770299B2

(12) United States Patent
Komuro et al.

(10) Patent No.: US 9,770,299 B2
(45) Date of Patent: Sep. 26, 2017

(54) TREATMENT TOOL, MANIPULATOR, AND SURGERY SUPPORT SYSTEM

(71) Applicant: OLYMPUS CORPORATION, Tokyo (JP)

(72) Inventors: Takahiro Komuro, Tokyo (JP); Masatoshi Iida, Tokyo (JP); Hirotaka Namiki, Tokorozawa (JP)

(73) Assignee: OLYMPUS CORPORATION, Tokyo (JP)

( * ) Notice: Subject to any disclaimer, the term of this patent is extended or adjusted under 35 U.S.C. 154(b) by 266 days.

(21) Appl. No.: 14/138,216

(22) Filed: Dec. 23, 2013

(65) Prior Publication Data
US 2014/0107667 A1 Apr. 17, 2014

Related U.S. Application Data

(63) Continuation of application No. PCT/JP2012/067027, filed on Jun. 27, 2012.

(30) Foreign Application Priority Data

Jun. 30, 2011 (JP) ................................. 2011-146796
Jun. 30, 2011 (JP) ................................. 2011-146797
May 22, 2012 (JP) ................................. 2012-116742

(51) Int. Cl.
*A61B 19/00* (2006.01)
*A61B 34/00* (2016.01)
(Continued)

(52) U.S. Cl.
CPC .............. *A61B 19/22* (2013.01); *A61B 34/30* (2016.02); *A61B 34/37* (2016.02); *A61B 34/70* (2016.02);
(Continued)

(58) Field of Classification Search
CPC ..... A61B 19/22; A61B 17/04; A61B 17/0469; A61B 17/28; A61B 17/282; A61B 17/29;
(Continued)

(56) References Cited

U.S. PATENT DOCUMENTS 4,500,780 A 2/1985 Buan et al.
7,540,867 B2 * 6/2009 Jinno ................................. 414/7
(Continued)

FOREIGN PATENT DOCUMENTS

JP 04-263831 A 9/1992
JP 11-010575 A 1/1999
(Continued)

OTHER PUBLICATIONS

Extended Supplementary European Search Report dated Jul. 17, 2015 from related European Application No. 12 80 5135.6.
(Continued)

*Primary Examiner* — Melanie Tyson
(74) *Attorney, Agent, or Firm* — Scully, Scott, Murphy & Presser, P.C.

(57) ABSTRACT

A treatment tool of which a treatment unit operates with a driving force generated from a driving source includes a driving force transmission member that is connected to the driving source, a connecting portion that is formed in the treatment unit, that is connected to the driving wire, that is supplied with the driving force from the driving source via the driving force transmission member, and that converts the driving force into movement of the treatment unit, and a member for detecting amount of movement that is moved by the connecting portion.

10 Claims, 10 Drawing Sheets

(51) Int. Cl.
*A61B 90/50* (2016.01)
*A61B 34/30* (2016.01)
*A61B 34/37* (2016.01)
*A61B 17/29* (2006.01)
*A61B 90/00* (2016.01)

(52) U.S. Cl.
CPC .............. *A61B 34/71* (2016.02); *A61B 34/77* (2016.02); *A61B 90/50* (2016.02); *A61B 2017/2927* (2013.01); *A61B 2034/305* (2016.02); *A61B 2090/061* (2016.02)

(58) Field of Classification Search
CPC .... A61B 2017/0609; A61B 2017/2912; A61B 2017/2926; A61B 2017/2927; A61B 2017/2929; A61B 2017/293; A61B 2017/2932; A61B 18/1442; A61B 10/06
See application file for complete search history.

(56) References Cited

U.S. PATENT DOCUMENTS

| | | | |
|---|---|---|---|
| 2009/0031842 A1* | 2/2009 | Kawai | A61B 17/29 74/490.01 |
| 2010/0082041 A1 | 4/2010 | Prisco | |
| 2010/0241135 A1* | 9/2010 | Iida | A61B 34/71 606/130 |
| 2011/0009698 A1 | 1/2011 | Ashida et al. | |

FOREIGN PATENT DOCUMENTS

| | | |
|---|---|---|
| JP | 11-077577 A | 3/1999 |
| JP | 2000-181618 A | 6/2000 |
| JP | 2005-028018 A | 2/2005 |
| JP | 2005-349489 A | 12/2005 |
| JP | 2007-290058 A | 11/2007 |
| JP | 2008-253463 A | 10/2008 |
| JP | 2010-220684 A | 10/2010 |
| JP | 2010-220685 A | 10/2010 |
| JP | 2011-089797 A | 5/2011 |
| WO | WO 00/40419 A1 | 7/2000 |

OTHER PUBLICATIONS

International Search Report dated Aug. 14, 2012 issued in PCT/JP2012/067027.

Japanese Office Action dated Feb. 16, 2016 in Japanese Patent Application No. 2012-116742.

* cited by examiner

TREATMENT TOOL, MANIPULATOR, AND SURGERY SUPPORT SYSTEM

This application is a continuation application based on PCT Patent Application No. PCT/JP2012/067027, filed Jun. 27, 2012, claiming priority based on Japanese Patent Application No. 2011-146796, filed Jun. 30, 2011, Japanese Patent Application No. 2011-146797, filed Jun. 30, 2011, and Japanese Patent Application No. 2012-116742, filed May 22, 2012, the contents of which are incorporated herein by reference.

BACKGROUND OF THE INVENTION

Field of the Invention

The present invention relates to a treatment tool, a manipulator, and a surgery support system.

Description of Related Art

In the past, a surgery support system having a manipulator in which a treatment tool is mounted on a remotely-controllable arm was known as a system for supporting a surgical operation.

A movable portion such as a joint is formed in the manipulator and the manipulator is displaced to a desired orientation by causing the movable portion to move. The movable portion of the manipulator is controlled to have the desired orientation through the use of a driving source and a power transmission member transmitting power to the movable portion and detection means for detecting the amount of movement of the movable portion.

For example, Japanese Unexamined Patent Application, First Publication H04-263831 discloses a detection device including an endoscope insertion part having a flexural portion, a wire transmitting power for causing the flexural portion to move in a flexural manner, and displacement detecting means for detecting the amount of displacement of the wire.

Japanese Unexamined Patent Application, First Publication 2010-220684 discloses a displacement detecting mechanism including a power transmission wire causing a joint to move, a displacement sensing wire connected to the power transmission wire so as to detect the amount of displacement of the joint, and a sensor detecting the amount of movement of the displacement sensing wire.

SUMMARY OF THE INVENTION

According to a first aspect of the invention, a treatment tool of which a treatment unit operates with a driving force generated from a driving source, the treatment tool includes: a driving force transmission member that is connected to the driving source; a connecting portion that is formed in the treatment unit, that is connected to the driving force transmission member, that is supplied with the driving force from the driving source via the driving force transmission member, and that converts the driving force into movement of the treatment unit; and a member for detecting amount of movement that is moved by the connecting portion.

According to a second aspect of the invention, in the treatment tool according to the first aspect, the connecting portion may include a connecting member to which the member for detecting amount of movement is fixed.

According to a third aspect of the invention, in the treatment tool according to the second aspect, the connecting member may include a turning portion that turns about a predetermined support point, wherein the driving force transmission member may be fixed to a position on the connecting member which is separated from the predetermined support point by a first distance, and the member for detecting amount of movement may be fixed to a position on the connecting member which is separated from the predetermined support point by a second distance greater than the first distance.

According to a fourth aspect of the invention, in the treatment tool according to the third aspect, the driving force transmission member and the member for detecting amount of movement may be linear members, wherein the turning portion may include: a first pulley of which a rotation center is the predetermined support point and in which the driving force transmission member is wound on an outer periphery thereof; and a second pulley of which the rotation center may be coaxial with the rotation center of the first pulley, that has a diameter larger than that of the first pulley, and in which the member for detecting amount of movement may be wound on an outer periphery thereof, and wherein the member for detecting amount of movement may be fixed to the second pulley.

According to a fifth aspect of the invention, the treatment tool according to any one of the second to fourth aspects, may further include: a driving guide member that guides the driving force transmission member; a detecting guide member that guides the member for detecting amount of movement; and a support member that fixes and supports the driving guide member and the detecting guide member.

According to a sixth aspect of the invention, in the treatment tool according to the fifth aspect, the support member may fix and support the driving guide member so that the driving force transmission member extending from the driving guide member to the connecting member has a linear shape extending from a distal end of the driving guide member to a contact point between the driving force transmission member and the connecting member, and may fix and support the detecting guide member so that the member for detecting amount of movement extending from the detecting guide member to the connecting member has a linear shape extending from a distal end of the detecting guide member to a contact point between the member for detecting amount of movement and the connecting member.

According to a seventh aspect of the invention, in the treatment tool according to the fifth aspect or sixth aspect, the support member may fix and support the driving guide member and the detecting guide member so that the driving force transmission member and the member for detecting amount of movement are parallel to each other between the driving guide member and the connecting member and between the detecting guide member and the connecting member.

According to an eighth aspect of the invention, in the treatment tool according to the first aspect, the connecting portion may include: a first connecting member that is formed in the treatment unit, that is connected to the driving force transmitting member, that is supplied with the driving force from the driving source via the driving force transmission member, and that converts the driving force into the movement of the treatment unit; and a second connecting member that is formed in the treatment unit, that is connected to the first connecting member, and that is moved by the treatment unit moving by the driving force, and wherein the member for detecting amount of movement may be fixed to the second connecting member.

According to a ninth aspect of the invention, in the treatment tool according to the eighth aspect, the member for detecting amount of movement may be moved by the second connecting member in a direction in which the driving force transmission member moves to transmit the driving force, and wherein the treatment tool may further include an amplification mechanism that amplifies an amount of movement of the member for detecting amount of movement at a predetermined ratio relative to an amount of movement of the driving force transmission member.

According to a tenth aspect of the invention, in the treatment tool according to the ninth aspect, the first connecting member may turn about a predetermined first support point, wherein the second connecting member rotationally may move about a predetermined second support point, wherein the driving force transmission member may be fixed to a position on the first connecting member which is separated from the first support point by a first distance, and wherein the member for detecting amount of movement may be fixed to a position on the second connecting member which is separated from the second support point by a second distance greater than the first distance.

According to an eleventh aspect of the invention, in the treatment tool according to the tenth aspect, the driving force transmission member and the member for detecting amount of movement may be linear members, the first connecting member may be a first pulley of which a rotation center is the first support point and in which the driving force transmission member may be wound on an outer periphery thereof, the second connecting member may be a second pulley of which a rotation center may be the second support point and in which the member for detecting amount of movement may be wound on an outer periphery thereof, and the member for detecting amount of movement member may be fixed to the second pulley.

According to a twelfth aspect of the invention, the treatment tool according to any one of the eighth to eleventh aspects, may further include: a driving guide member that guides the driving force transmission member; a detecting guide member that guides the member for detecting amount of movement; and a support member that fixes and supports the driving guide member and the detecting guide member.

According to a thirteenth aspect of the invention, in the treatment tool according to the twelfth aspect, the support member may fix and support the driving guide member so that the driving force transmission member extending from the driving guide member to the first connecting member has a linear shape extending from a distal end of the driving guide member to a contact point between the driving force transmission member and the first connecting member, and may fix and support the detecting guide member so that the member for detecting amount of movement extending from the detecting guide member to the second connecting member has a linear shape extending from a distal end of the detecting guide member to a contact point between the member for detecting amount of movement and the second connecting member.

According to a fourteenth aspect of the invention, in the treatment tool according to the twelfth aspect or thirteenth aspect, the support member may fix and support the driving guide member and the detecting guide member so that the driving force transmission member and the member for detecting amount of movement are parallel to each other between the driving guide member and the first connecting member and between the detecting guide member and the second connecting member.

According to a fifteenth aspect of the invention, in the treatment tool according to any one of the first to fourteenth aspects, a bending part in which the driving force transmission member and the member for detecting amount of movement are both bent may be formed between the treatment unit and the driving source, the bending part may rotationally move in a treatment unit side about a predetermined bending axis relative to a driving source side, and the driving force transmission member and the member for detecting amount of movement may be arranged such that distances from the bending axis are substantially equal to each other at vicinity of the bending axis.

According to a sixteenth aspect of the invention, in the treatment tool according to any one of the first to fifteenth aspects, the driving force transmission member and the member for detecting amount of movement may be wires.

According to a seventeenth aspect of the invention, a manipulator includes: the above-mentioned treatment tool; and an arm that has the treatment tool mounted thereon.

According to an eighteenth aspect of the invention, there is provided a surgery support system including the above-mentioned treatment tool.

DETAILED DESCRIPTION OF THE INVENTION

First Embodiment

Figure 1:
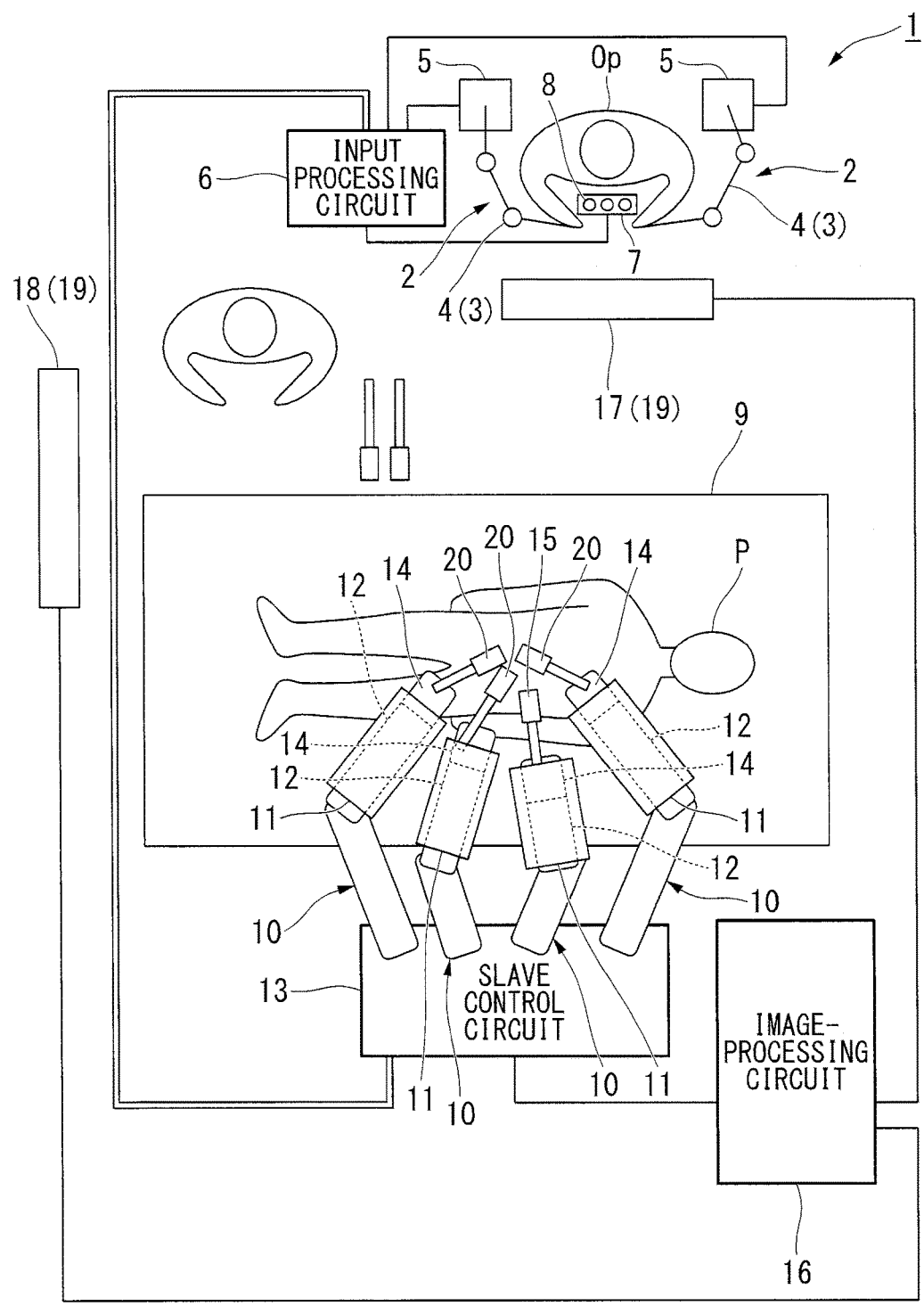
FIG. 1 is a diagram schematically illustrating the configuration of a surgery support system according to a first embodiment of the invention.

A treatment tool, a manipulator, and a surgery support system according to a first embodiment of the invention will be described below. FIG. 1 is a diagram illustrating the overall configuration of a surgery support system according to the first embodiment of the invention. The configuration of the surgery support system 1 according to this embodiment will be described below.

As shown in FIG. 1, the surgery support system 1 according to this embodiment is a master-slave type system including two types of arms consist of a master arm 2 and a slave arm 10 and remotely controlling the slave arm 10 to follow the operation of the master arm 2. The surgery support system 1 is provided with a treatment tool 20 (see FIG. 2) treating a patient P.

The surgery support system 1 includes a master arm 2, an input processing circuit 6, a switch 7, an operating table 9, a slave arm 10 (manipulator), a slave control circuit 13, an image-processing circuit 16, and a display 19.

The master arm 2 includes a plurality of link mechanism 3. Each link mechanism 3 has a structure in which a plurality of link member 4 are connected to each other. A position detector 5 such as an incremental encoder is provided in the respective link member 4 constituting each link mechanism 3.

The position detector 5 provided in the master arm 2 is configured to detect the movement of the each link member 4 and output a detection signal to the input processing circuit 6. The detection signal output from the position detectors 5 are input to the input processing circuit 6 and the amount of manipulation of the master arm 2 is detected by the input processing circuit 6 based on the detection signals.

The master arm 2 and the switch 7 are electrically connected to the input processing circuit 6. The switch 7 is used to select the slave arm 10 operating correspondingly the operation of the master arm 2. The input processing circuit 6 detects the amount of manipulation of the master arm 2, generates a signal for manipulating the slave arm 10 based on the detected amount of manipulation, and outputs the generated signal to the slave control circuit 13.

The switch 7 includes, for example, a plurality of push button 8 corresponding to the slave arms 10 and outputs a selection signal corresponding to the pressed push button 8 to the input processing circuit 6.

Manipulation members such as a scaling changing switch used to change the movement ratio of the master arm 2 and the slave arm 10 or a foot switch used to emergently stop the system may be connected to the input processing circuit 6.

The operating table 9 is a table on which a patient P to be observed or treated is placed. The slave arm 10 is installed in the vicinity of the operating table 9. In this embodiment, a plurality of slave arm 10 are provided for a single operating table 9.

Each slave arm 10 includes a plurality of multi-degree-of-freedom joint 11. By flexing the multi-degree-of-freedom joint 11, the treatment tool 20 or the like attached to the distal end side (the end facing the body cavity of the patient P) of the respective slave arm 10 is positioned relative to the patient P placed on the operating table 9.

Each multi-degree-of-freedom joint 11 is independently driven by a power supply not shown. A motor (servo motor), for example, having a servo mechanism including an incremental encoder or a decelerator can be employed as the power supply. The movement of the multi-degree-of-freedom joint 11 through the power supply is controlled by the slave control circuit 13.

The orientations or positions of the slave arm 10 is detected by a slave arm position detector 12 connected to the power supply. The slave arm position detector 12 detects the amount of driving of the power supply and outputs a detection signal to the slave control circuit 13. The detection signal output from the slave arm position detector 12 is input to the slave control circuit 13 and the amount of driving of the slave arms 10 is detected by the slave control circuit 13 based on the detection signal.

Each slave arm 10 is provided with a plurality of driving source 21 (see FIG. 2) driving the treatment tool 20 attached to the corresponding slave arm 10 independently of the power supply driving the multi-degree-of-freedom joints 11.

A surgical power transmission adapter 14 connecting the slave arm 10 to the treatment tool 20 is formed at the distal end of the slave arm 10. The surgical power transmission adapter 14 is a member being interposed between the slave arm 10 and the treatment tool 20 and having a mechanism transmitting the power from the slave arm 10 to the treatment tool 20 through a translational motion.

The slave control circuit 13 is configured to include, for example, a CPU and a memory. The slave control circuit 13 stores a predetermined program for controlling the slave arm 10 and controls the movement of the slave arm 10 or the treatment tool 20 in accordance with a control signal from the input processing circuit 6.

Specifically, the slave control circuit 13 specifies the slave arm 10 or the treatment tool 20 (hereinafter, referred to as a "slave arm 10 and the like") to be manipulated through the use of the master arm 2 manipulated by an operator Op based on the control signal from the input processing circuit 6. The slave control circuit 13 generates a driving signal for causing the slave arm 10 and the like to move. The slave control circuit 13 outputs the driving signal to the power supply of the slave arm 10. And the slave control circuit 13 controls the magnitude or polarity of the driving signal so that the slave arm 10 reaches the movement target based on the detection signal output from the position detector 5 of the power supply in correspondence with the movement of the slave arm 10. Accordingly, the slave control circuit 13 can control the movement of the slave arm 10 and the like specified as a target to be manipulated through the master arm 2.

In the surgery support system 1 according to this embodiment, the slave arm 10 operating in correspondence with the manipulation of the master arm 2 is specified and then the specified slave arm 10 is made to move. Accordingly, more slave arms 10 than the number of master arms 2 can be switched and manipulated. For example, in this embodiment, four slave arms 10 can be manipulated using two master arms 2. The number of master arms 2 and the number of slave arms 10 may be equal to each other.

In this embodiment, an observation mechanism 15 acquiring an image of a treatment target is attached to at least one of a plurality of the slave arm 10. A known observation mechanism 15 such as a medical endoscope can be appropriately employed as the observation mechanism 15. In this embodiment, the image acquired by the observation mechanism 15 is output as an image signal to the image processing circuit 16 via the slave control circuit 13.

The image processing circuit 16 performs an image process on the image signal output from the slave control circuit 13 and generates image data to be displayed on the display 19 (an operator display 17 or an assistant display 18). The operator display 17 and the assistant display 18 are consisted, for example, by a liquid crystal display and display an image based on the image data generated by the image processing circuit 16.

Figure 2:
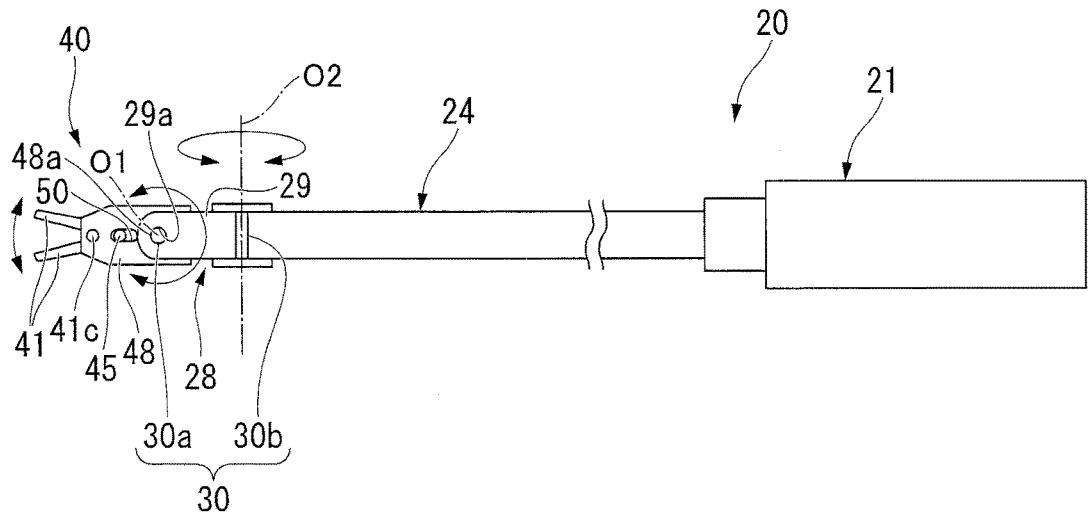
FIG. 2 is a side view illustrating a treatment tool provided to the surgery support system.
Figure 3:
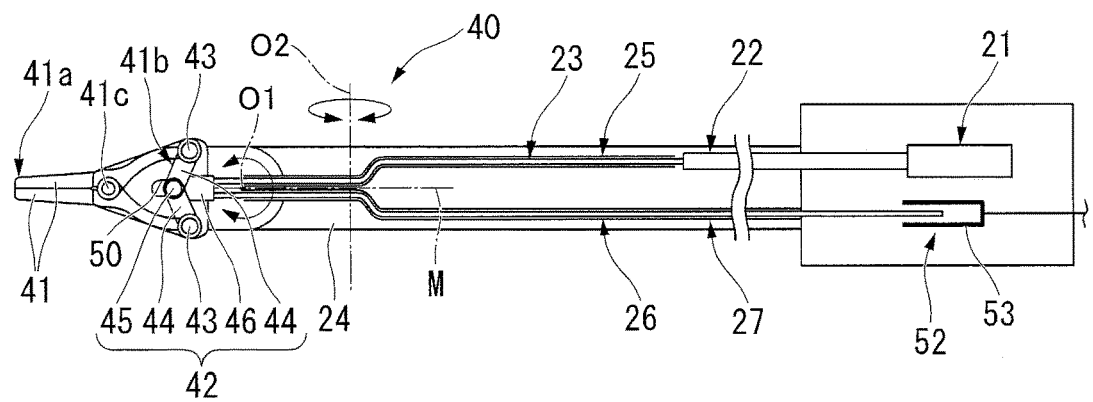
FIG. 3 is a cross-sectional view of the treatment tool shown in FIG. 2.
Figure 4:
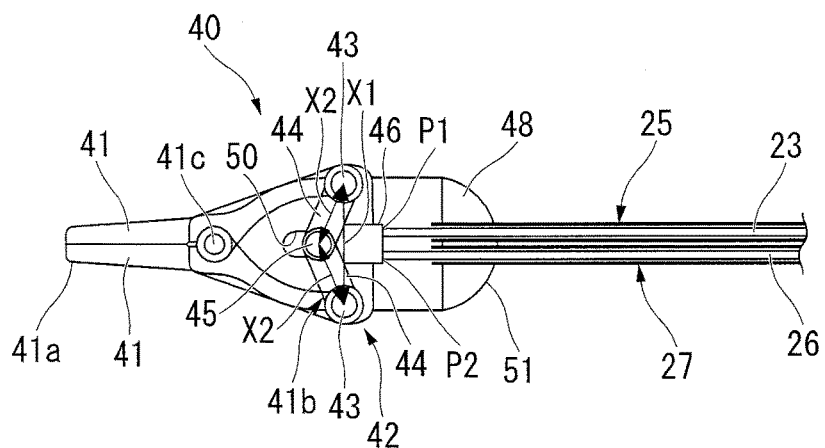
FIG. 4 is an enlarged cross-sectional view of a distal end of a treatment unit in the treatment tool shown in FIG. 2.

FIG. 2 is a side view illustrating the treatment tool 20 installed in the surgery support system 1. FIG. 3 is a cross-sectional view of the treatment tool 20. FIG. 4 is an enlarged cross-sectional view of the distal end of a treatment unit in the treatment tool 20. As shown in FIGS. 2 and 3, the treatment tool 20 is a so-called surgical instrument and includes a driving source 21, a body section 24, a treatment unit 40 having a bending part 28, and a displacement detecting mechanism 52.

The driving source 21 includes, for example, a servo motor. The driving source 21 is controlled by the slave control circuit 13 and generates a driving force for operating the treatment unit 40. An end of a rod 22 is fixed to the driving source 21. The driving source 21 causes the rod 22 to move forward and backward in the direction of the central axis line of the rod 22. The other end of the rod 22 is located closer to the driving source 21 side than the bending part 28. An end of a flexible driving wire 23 is fixed to the other end of the rod 22. The other end of the driving wire 23 is connected to a connecting member 42 to be described later. The driving wire 23 and the connecting member 42 are fixed to each other, for example, by welding. The driving force transmission member of this embodiment is composed of the rod 22 and the driving wire 23 and connected to the driving source 21. The driving force generated from the driving source 21 is transmitted to the treatment unit 40 via the driving force transmission member.

The body section 24 has a cylindrical shape of which both ends are opened. An end of the body section 24 is fixed to the driving source 21 and the other end thereof is fixed to the bending part 28. The rod 22 and the driving wire 23 described above, a driving guide member 25 through which the driving wire 23 is inserted, a sensing wire 26 (member for detecting amount of movement), and a detecting guide member 27 through which the sensing wire 26 is inserted are formed in the body section 24.

The driving guide member 25 is a cylindrical member defining the path of the driving wire 23 in the body section 24 and guiding the driving wire 23. The driving guide member 25 is formed of, for example, a coil pipe.

The sensing wire 26 is a wire of which an end is fixed to a fixing portion 46 to be described later and the other end is arranged in the driving source 21. In this embodiment, the sensing wire 26 is formed of a metal wire.

The detecting guide member 27 is a cylindrical member defining the path of the sensing wire 26 in the body section 24 and guiding the sensing wire 26. The detecting guide member 27 is formed of, for example, a coil pipe or a metal pipe. The inner surface of the detecting guide member 27 and the outer surface of the sensing wire 26 may be subjected to surface treatment for reducing the mutual friction.

The driving guide member 25 and the detecting guide member 27 are arranged separately from each other so as not to interfere with each other and are parallel to each other in the bending part 28.

The bending part 28 includes an intermediate support member 29 formed substantially in a cylindrical shape and two axes 30 (a first bending axis 30a and a second bending axis 30b) arranged at both ends of the intermediate support member 29. The bending axes 30 are arranged in a state where the first bending axis 30a and the second bending axis 30b form an angle of 90 degrees. In this embodiment, the bending axis 30 (the first bending axis 30a) arranged on the side close to the distal end of the treatment unit 40 is parallel to an opening and closing axis 41c to be described later for causing the treatment unit 40 to perform an opening and closing operation.

Figure 5:
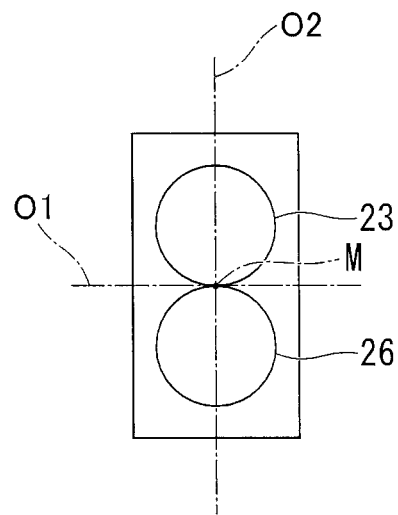
FIG. 5 is a diagram schematically illustrating the positional relationship between a driving wire and a sensing wire in the treatment tool shown in FIG. 2.

FIG. 5 is a diagram schematically illustrating the positional relationship between the driving wire 23 and the sensing wire 26 in the treatment tool 20. As shown in FIGS. 2, 3 and 5, the driving wire 23 and the sensing wire 26 are arranged to be parallel to each other in the vicinity of the first bending axis 30a and the second bending axis 30b. The intermediate line M between the driving wire 23 and the sensing wire 26 parallel to each other intersects the central axis line O1 of the first bending axis 30a and intersects the central axis line O2 of the second bending axis 30b. By employing this positional relationship, in the vicinity of the first bending axis 30a close to the fixing portion 46, it is possible to prevent the bending radii of flexion of the driving wire and the sensing wire from being different depending on the direction of bending. Therefore, the influences of the bending of the bending part 28 on the wires can be prevented from being different depending on the direction of bending. In the specification, for the purpose of easy understanding of the driving wire 23 and the sensing wire 26, the driving wire 23 and the sensing wire 26 which should be shown to overlap with each other in practice are shown to be separated in the vertical direction of the drawing paper.

As shown in FIGS. 2 and 3, the bending part 28 is bent so that the distal end of the treatment unit 40 rotationally moves about two bending axes 30 relative to the driving source 21 side by a bending wire (not shown) arranged in the body section 24 and a driving source (not shown) provided independently of the driving source 21.

The treatment unit 40 includes a pair of jaws 41 mutually rotationally moving about the opening and closing axis 41c, a connecting member (connecting portion) 42 connected to the pair of jaws 41, and a support member 48 supporting the pair of jaws 41 through the opening and closing axis 41c and being attached to the first bending axis 30a so as to be rotatable about the central axis line of the first bending axis 30a.

The pair of jaws 41 is provided, for example, for the purpose of clamping a tissue of a patient P (see FIG. 1) or clamping a suture thread or needle. Each of the pair of jaws 41 has a bent shape in the part of the opening and closing axis 41c and both are arranged to face each other.

As shown in FIG. 4, the connecting member 42 includes a pair of links 44 and a fixing portion 46. The pair of links 44 is rotatably connected to each end portion 41b (proximal end portions of the pair of jaws 41) of the pair of jaws 41 located close to the bending part 28 side through the use of pins 43. The fixing portion 46 is rotatably connected to each of the pair of links 44 through the pin 45. The pins 43 and the pins 46 are substantially cylindrical members of which the central axis line extends parallel to the opening and closing axis 41c. The pins 43 couples the pair of jaws 41 to the pair of links 44 respectively. The pin 45 couples the pair of links 44 to the fixing portion 46 respectively.

An end of the driving wire 23 constituting the driving force transmission member and an end of the sensing wire 26 are fixed to the fixing portion 46. The fixing position P1 of the fixing portion 46 and the driving wire 23 and the fixing position P2 of the fixing portion 46 and the sensing wire 26 are arranged in the direction (see FIG. 2) in which the second bending axis 30b of the bending part 28 extends.

In this embodiment, the pins 43 fixing the pair of jaws 41 and the pair of links 44 are arranged at a position (on the proximal end side) closer to the bending part 28 than the pin 45 connecting the pair of links 44 to the fixing portion 46. Accordingly, when the fixing portion 46 moves to the bending part 28 side (the proximal end side), the proximal ends of the pair of jaws 41 are moved so that a distance of the pins 43 from each other gets long. The distance X1 between the pins 43 in the state where the pair of jaws 41 is closed is set to be smaller than double the distance X2 between the pins 43 and the pin 45. Accordingly, even when the fixing portion 46 moves closer to the bending part 28, the pin 45 does not move closer to the bending part 28 (the proximal end) than the pins 43 do. At this time, a force for clamping a target is applied by the facing surfaces of the distal ends 41a of the jaws 41.

The pair of links 44 connected to each other with the pins 43 and the pin 45 constitutes a toggle mechanism (a leverage mechanism). Accordingly, when the driving wire 23 is pulled to close the distal ends 41a of the jaws 41, the driving force transmitted via the driving wire 23 is decelerated by the toggle mechanism and is output to the pair of jaws 41. As a result, the jaws 41 can be closed with a force greater than the driving force generated from the driving source 21.

The pair of links 44 and the fixing portion 46 are, for example, members having substantially the same rigidity as the pair of jaws 41 and do not deformed with the driving force transmitted via the driving wire 23.

In this way, the coupling member 42 serves as a link converting the driving force transmitted from the driving source 21 via the rod 22 and the driving wire 23 into the movement of the treatment unit 40.

The support member 48 includes an axis support portion 49, a long hole portion 50, and a guide fixing portion 51. The axis support portion 49 supports both ends of the opening and closing axis 41c. The long hole portion 50 movably supports the pin 45 provided in the fixing portion 46. The guide fixing portion 51 fixes and supports the driving guide member 25 and the detecting guide member 27. In this embodiment, a pair of cylindrical protrusions 48a which becomes the first bending axis 30a of the bending part 28 is formed on the outer surface of the support member 48. A hole 29a (see FIG. 2) through which the protrusion 48a formed in the support member 48 is inserted is formed in the intermediate support member 29 of the bending part 28.

The guide fixing portion 51 fixes and supports the driving guide member 25 so that the driving wire 23 extending from the driving guide member 25 to the fixing portion 46 has a linear shape extending from the end of the driving guide member 25 to the fixing position P1. The guide fixing portion 51 fixes and supports the detecting guide member 27 so that the sensing wire 26 extending from the detecting guide member 27 to the fixing portion 46 has a linear shape extending from the end of the detecting guide member 27 to the fixing position P2. The guide fixing portion 51 fixes and supports the driving guide member 25 and the detecting guide member 27 so that the driving wire 23 and the sensing wire 26 are parallel to each other between the driving guide member 25 and the fixing portion 46 and between the detecting guide member 27 and the fixing portion 46.

As shown in FIG. 3, the displacement detecting mechanism 52 includes a sensor 53 detecting the amount of displacement of the base end (an end not fixed to the fixing portion 46) of the sensing wire 26 and an output unit (not shown) outputting the amount of displacement detected by the sensor 53. The sensor 53 of the displacement detecting mechanism 52 is a magnetic sensor detecting a variation in magnetism due to the variation in position of the sensing wire 26 formed of a metal wire relative to the sensor 53. The amount of displacement of the sensing wire 26 detected by the sensor 53 varies to correspond to the opening and closing of the pair of jaws 41. Accordingly, the sensor 53 can detect the opened or closed state of the pair of jaws 41 by detecting the amount of displacement of the sensing wire 26.

The output unit of the displacement detecting mechanism 52 outputs the amount of displacement detected by the sensor 53 to the slave control circuit 13. The slave control circuit 13 controls the driving state of the driving source 21 based on the amount of displacement output from the output unit of the displacement detecting mechanism 52.

The operations of the treatment tool 20, the slave arm 10 (manipulator), and the surgery support system 1 according to this embodiment will be described below.

The surgery support system 1 is used in a state where the treatment tool 20 is mounted on the slave arm 10. An operator Op of the surgery support system 1 manipulates the master arm 2 to remotely manipulate the slave arm 10 and the treatment tool 20. When using the treatment tool 20, the driving source 21 is driven by the slave control circuit 13 and the rod 22 connected to the driving source 21 advances and retracts. Then, the driving wire 23 fixed to the rod 22 also advances and retracts along with the rod 22 and the fixing portion 46 fixed to the driving wire 23 also advances and retracts. By causing the fixing portion 46 to advance and retract, the pair of jaws 41 is opened and closed.

When operating to close the pair of jaws 41, the driving wire 23 is pulled by the driving source 21 and thus the pulling force is applied to the driving wire 23. The driving wire 23 to which the pulling force is applied may be slightly stretched by the pulling force. Accordingly, there is a possibility of causing a difference between the amount of pulling of the driving wire 23 actually pulled by the driving source 21 and the amount of pulling by which the driving wire 23 pulls the fixing portion 46 depending on the amount of stretching of the driving wire 23. Particularly, in the state where a tissue to be treated is clamped by the distal ends of the pair of jaws 41, the difference due to the stretching of the driving wire 23 becomes more marked by applying a strong pulling force for clamping the tissue to the driving wire 23.

When the fixing portion 46 is pulled by the driving wire 23, the sensing wire 26 fixed to the fixing portion 46 is pushed to the driving source 21. The sensing wire 26 only moves by the fixing portion 46 and is fixed to only the fixing portion 46. Accordingly, a force causing the stretching of the sensing wire 26 is not applied to the sensing wire 26. Accordingly, the sensing wire 26 moves to correspond to the amount of displacement of the fixing portion 46 without being affected by the stretching of the driving wire 23.

The sensor 53 of the displacement detecting mechanism 52 detects the amount of displacement of the sensing wire 26 and the slave control circuit 13 receiving the output from the sensor 53 detects the opened and closed state of the pair of jaws 41. At this time, the opened and closed state of the pair of jaws 41 detected by the slave control circuit 13 is not affected by the difference between the amount of pulling of the driving wire 23 and the amount of movement of the fixing portion 46 which is caused by the stretching of the driving wire 23. That is, the opened and closed state of the pair of jaws 41 is detected with a high precision.

When the treatment tool 20 is used, the pair of jaws 41 may be opened and closed in a state where the bending part 28 bends. In this case, the driving wire 23 and the sensing wire 26 both flexes at the bending axis 30. In this embodiment, in both the state where the bending part 28 flexes and the state where the bending part 28 linearly extends, both the path length of the driving wire 23 and the path length of the sensing wire 26 at the bending part 28 are not changed. Accordingly, by detecting the amount of displacement of the sensing wire 26 without depending on the bending state of the bending part 28, it is possible to detect the opened and closed state of the pair of jaws 41 with a high precision.

As described above, in the treatment tool 20, the slave arm 10 (manipulator), and the surgery support system 1 according to this embodiment, the driving wire 23 and the sensing wire 26 are independently fixed to the fixing portion 46 of the coupling member 42 opening and closing the pair of jaws 41. Accordingly, the operation of the pair of jaws 41 is precisely reflected in the displacement of the sensing wire 26 without being affected by the stretching of the driving wire 23. As a result, it is possible to detect the amount of displacement of the pair of jaws 41 provided in the treatment unit 40 with a high precision.

Second Embodiment

Figure 6:
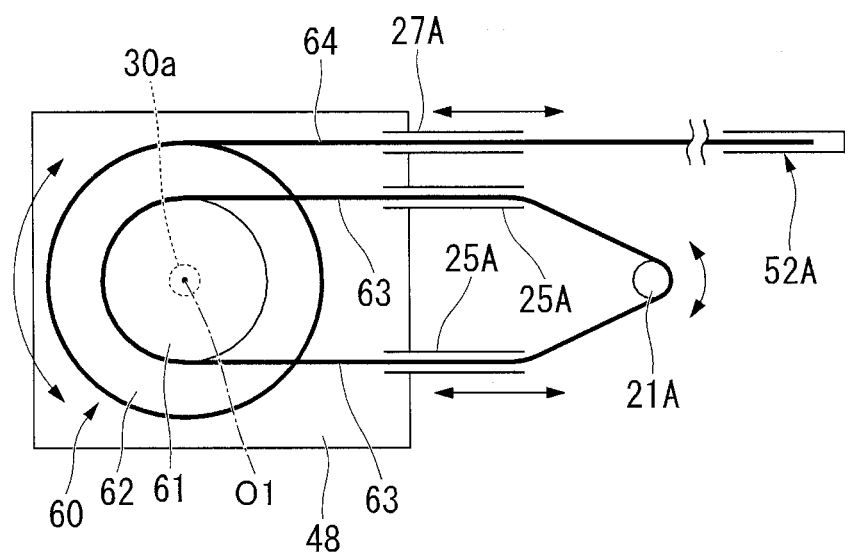
FIG. 6 is a diagram schematically illustrating a partial configuration of the treatment tool in a treatment tool, a manipulator, and a surgery support system according to a second embodiment of the invention.

A treatment tool, a manipulator, and a surgery support system according to a second embodiment of the invention will be described below. In embodiments described below, the same elements as in the treatment tool 20, the manipulator (slave arm 10), and the surgery support system 1 according to the first embodiment will be referenced by the same symbols and description thereof will be omitted. FIG. 6 is a diagram schematically illustrating a partial configuration of the treatment tool of the treatment tool, the manipulator, and the surgery support system according to this embodiment.

In this embodiment, a mechanism for bending the bending part 28 will be described in detail.

As shown in FIG. 6, the first bending axis 30a is formed of a multi-stage pulley 60 having a shape in which two pulleys (a first pulley 61 and a second pulley 62) having different diameters are coaxially superimposed. The first bending axis 30a is supported by the intermediate support member 29 (see FIG. 2) so as to be rotatable about the rotation axis of the multi-stage pulley 60 and is fixed to the support member 48.

A bending wire 63 for rotating the multi-stage pulley 60 is wound on the small-diameter pulley (the first pulley 61) in the multi-stage pulley 60. A part of the bending wire 63 is fixed to a part of the outer peripheral surface of the first pulley 61 so that the first pulley 61 and the bending wire 63 do not slide relative to each other. A bending detecting wire 64 of which an end is fixed to the multi-stage pulley 60 is wound on the outer periphery of the large-diameter pulley (the second pulley 62) of the multi-stage pulley 60.

The bending wire 63 is connected to a driving source 21A provided independently of the driving source 21 described in the first embodiment. In this embodiment, a servo motor or the like having a rotational output shaft on which the bending wire 63 is wound can be employed as the driving source 21A.

The bending detecting wire 64 is a wire of which the amount of displacement is detected by the same displacement detecting mechanism 52A same as the displacement detecting mechanism 52 described in the first embodiment. In this embodiment, the amount of rotation of the multi-stage pulley 60 is detected by the slave control circuit 13 based on the amount of displacement detected by the displacement detecting mechanism 52A.

The bending wire 63 is inserted into a bending guide member 25A same as the driving guide member 25. The bending detecting wire 64 is inserted into a bending detecting guide member 27A same as the detecting guide member. The bending guide member 25A and the bending detecting guide member 27A are both fixed to the support member 48. The bending wire 63 extending from the bending guide member 25A to the multi-stage pulley 60 and the bending detecting wire 64 extending from the bending detecting guide member 27A to the multi-stage pulley 60 both extend substantially straight to the contact point with the multi-stage pulley 60 along the tangential lines of the pulleys.

The operations of the treatment tool, the manipulator, and the surgery support system according to this embodiment will be described with a focus on the operation of the bending part 28. In this embodiment, the diameter of the second pulley 62 on which the bending detecting wire 64 is wound is larger than the diameter of the first pulley 61 on which the bending wire 63 is wound. Accordingly, when the multi-stage pulley 60 is rotated by the bending wire 63, the amount of displacement of the bending detecting wire 64 is larger than the amount of displacement of the bending wire 63. Similarly to the first embodiment, the amount of displacement of the bending detecting wire 64 is reflected in the degree of rotation of the multi-stage pulley 60 without being affected by the stretching of the bending wire 63 when a pulling force is applied to the bending wire 63.

The degree of rotation of the multi-stage pulley 60 represents the bending angle of the support member 48 that the multi-stage pulley 60 is fixed, to the intermediate support member 29. That is, in this embodiment, it is possible to detect the bending angle of the support member 48 to the intermediate support member 29 through the use of the bending detecting wire 64 with a high precision without being affected by the stretching of the bending wire 63 when a pulling force is applied to the bending wire 63.

In this embodiment, the bending wire 63 is fixed to the outer peripheral surface of the first pulley 61 having a small diameter by friction force with the rotation axis of the multi-stage pulley 60 as a support point. The bending detecting wire 64 is fixed to the outer peripheral surface of the second pulley 62 having a large diameter. Accordingly, the amount of displacement of the bending detecting wire 64 can be set to be larger than the amount of displacement of the bending wire 63 and it is thus possible to enhance a detection resolution in the displacement detecting mechanism 52A. By optimizing the ratio of the diameters of the pulleys constituting the multi-stage pulley 60, a region in which the detectable range (dynamic range) of the displacement detecting mechanism 52A is wide can be used for the detection and it is thus possible to enhance the detection precision with little influence by noise or the like.

A configuration employing the multi-stage pulley 60 can be applied to the second bending axis 30b, similarly to this embodiment. A configuration employing the multi-stage pulley 60 can be applied to the opening and closing axis 41c, similarly to this embodiment.

Modified Example

Figure 7:
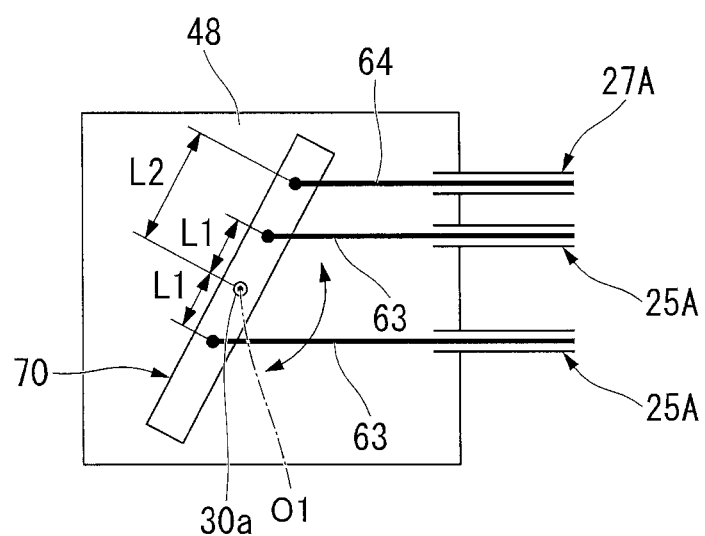
FIG. 7 is a diagram schematically illustrating the configuration of a modified example of the second embodiment.

A modified example of the second embodiment will be described below. FIG. 7 is a diagram schematically illustrating the configuration of a modified example.

This modified example is different from the second embodiment, in that the first bending axis 30a (see FIG. 2) employs a lever portion 70 extending in a direction perpendicular to the central axis line of the first bending axis 30a as shown in FIG. 7, instead of the multi-stage pulley 60 described in the second embodiment. The lever portion 70 uses the central axis line O1 of the first bending axis 30a as a support point and is fixed to the bending wire 63 at two points separated by the same distance (a first distance L1) from the support point in the length direction of the lever portion 70. The first distance L1 is distance between a fixing point where the bending wire 63 fixed to the lever portion 70 and the support point. The bending detecting wire 64 is fixed to the lever portion 70 at a position separated from the support point (the central axis line O1) by a second distance L2 which is larger than the first distance L1.

In this modified example, the same effects as in the second embodiment can be achieved. In this modified example, since the lever portion 70 has a rod shape, it is possible to make the configuration more compact than the disc-like multi-stage pulley 60 described in the second embodiment.

In this modified example, since the bending wire 63 is fixed to the lever portion 70, the first pulley 61 comes in contact with the bending wire 63 with a contact area smaller than the contact area between the first pulley 61 and the bending wire 63 in the second embodiment. Accordingly, the loss of a driving force due to friction is smaller.

Third Embodiment

A treatment tool, a manipulator, and a surgery support system according to a third embodiment of the invention will be described below. This embodiment is different from the above-mentioned embodiments, in that a treatment tool 120 has a configuration different from the treatment tool 20 described in the above-mentioned embodiments.

Figure 8:
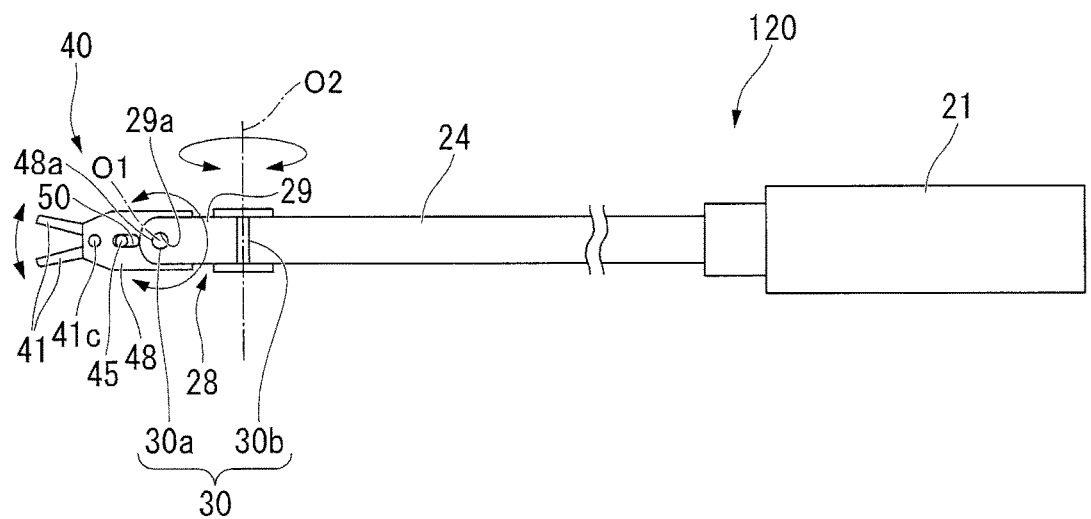
FIG. 8 is a side view illustrating a treatment tool provided to a surgery support system according to a third embodiment of the invention.
Figure 9:
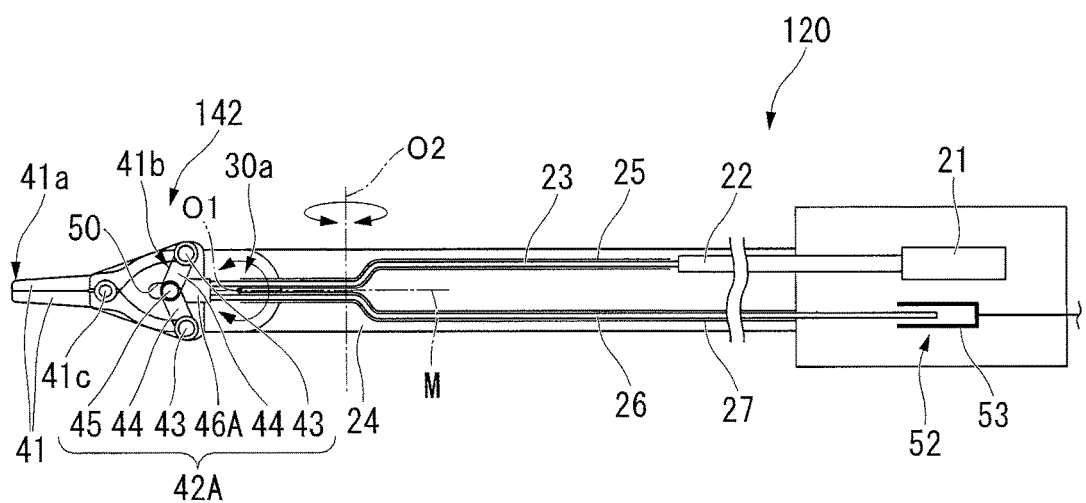
FIG. 9 is a cross-sectional view of the treatment tool shown in FIG. 8.
Figure 10A:
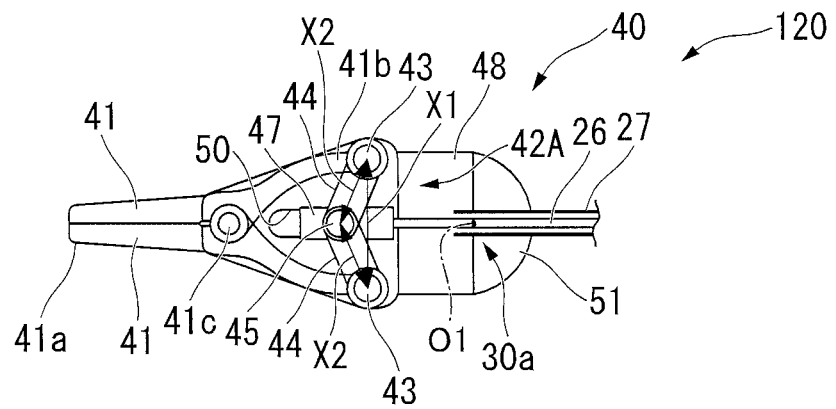
FIG. 10A is an enlarged side view of a treatment unit of the treatment tool shown in FIG. 8.
Figure 10B:
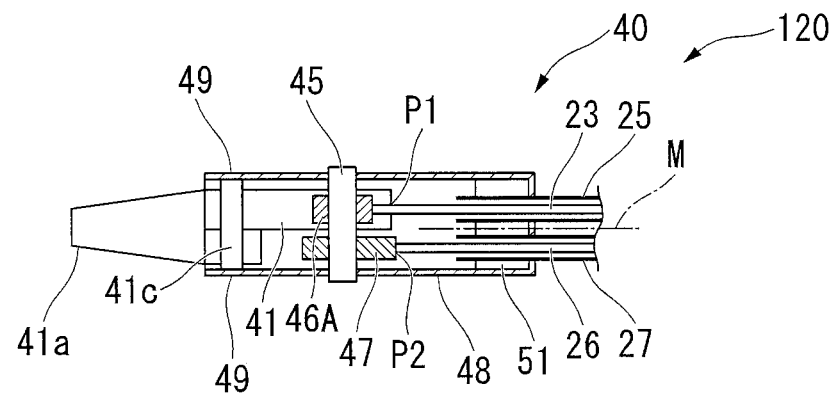
FIG. 10B is an enlarged bottom view of the treatment unit of the treatment tool shown in FIG. 8.

FIG. 8 is a side view illustrating the treatment tool 120 provided in the surgery support system 1. FIG. 9 is a cross-sectional view of the treatment tool 120. FIGS. 10A and 10B are enlarged views of the treatment unit 40, where FIG. 10A is a side view and FIG. 10B is a bottom view.

As shown in FIGS. 8 and 9, the treatment tool 120 is a so-called surgical instrument and includes a driving source 21, a body section 24, a treatment unit 40, and a displacement detecting mechanism 52. As shown in FIGS. 10A and 10B, the treatment unit 40 includes a connecting portion 142 connected to a pair of jaws 41 instead of the connecting portion 42 described in the first embodiment. In FIG. 9, for the purpose of easy understanding of the driving wire 23 and the sensing wire 26, the driving wire 23 and the sensing wire 26 which should be shown to overlap with each other in practice are shown to be separated in the vertical direction of the drawing paper.

The connecting portion 142 includes a connecting member 42A (first connecting member) and a sensing link 47 (second connecting member, see FIG. 10A).

The connecting member 42A includes a pair of links 44 described in the first embodiment and a fixing portion 46A rotatably connected to the pair of links 44 through the pin 45. An end of the driving wire 23 is fixed to the fixing portion 46A. This embodiment is different from the first embodiment, in that the sensing wire 26 is not fixed to the fixing portion 46A.

Figure 11:
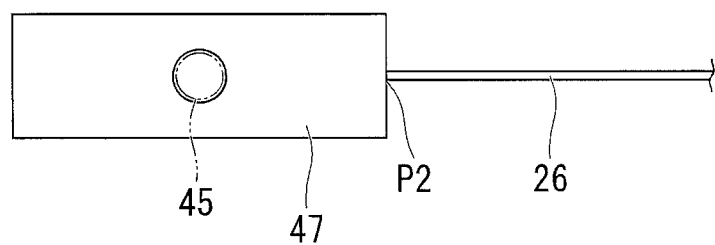
FIG. 11 is a side view illustrating the configuration of a sensing link provided in the treatment unit shown in FIG. 8.

FIG. 11 is a side view illustrating the configuration of the sensing link 47.

As shown in FIGS. 10B and 11, the sensing link 47 is a rigid body having a through-hole into which the pin 45 is inserted and is supplied with the driving force from the driving source 21 via the pin 45. For example, when the distal ends of the pair of jaws 41 is opened or closed with an external force other than the driving force from the driving source 21, the external force is transmitted to the pair of jaws 41, the pins 43, the pair of links 44, the pin 45, and the sensing link 47 in this order and the sensing 47 is moved.

As shown in FIG. 10B, since the sensing link 47 and the fixing portion 46A are connected through the pin 45, the sensing link 47 and the fixing portion 46A jointly move although a difference due to a slight margin. That is, when the pair of jaws 41 is opened or closed, the amount of displacement of the sensing link 47 is substantially equal to the amount of displacement of the fixing portion 46A.

The guide fixing portion 51 fixes and supports the driving guide member 25 so that the driving wire 23 extending from the driving guide member 25 to the fixing portion 46A has a linear shape extending from the distal end of the driving guide member 25 to the fixing position P1 on the fixing portion 46A. The guide fixing portion 51 fixes and supports the detecting guide member 27 so that the sensing wire 26 extending from the detecting guide member 27 to the sensing link 47 has a linear shape extending from the distal end of the detecting guide member 27 to the fixing position P2 on the sensing link 47. The guide fixing portion 51 fixes and supports the driving guide member 25 and the detecting guide member 27 so that the driving wire 23 and the sensing wire 26 are parallel to each other between the driving guide member 25 and the fixing portion 46A and between the detecting guide member 27 and the sensing link 47.

The operations of the treatment tool 120, the slave arm 10 (manipulator) and the surgery support system 1 will be described below with a focus on the differences from the first embodiment.

When the fixing portion 46A is pulled by the driving wire 23, the sensing link 47 connected to the fixing portion 46A via the pin 45 moves along with the fixing portion 46A. Since the fixing portion 46A and the sensing link 47 are connected through with the pin 45, a slight margin (clearance) is present between the fixing portion 46A and the sensing link 47, but the margin is much smaller than the amount of stretching of the driving wire 23 due to the pulling force applied to the driving wire 23.

The sensing wire 26 fixed to the sensing link 47 is pushed to the driving source 21 side. The sensing wire 26 is only moved by the sensing link 47 and is fixed to only the sensing link 47. Accordingly, a force causing the stretching of the sensing wire 26 is not applied to the sensing wire 26. The sensing wire 26 is moved to correspond to the amount of displacement of the sensing link 47 without being affected by the stretching of the driving wire 23. Since the amount of displacement of the sensing link 47 is substantially equal to the amount of displacement of the fixing portion 46A, the sensing wire 26 can be said to move to correspond to the amount of displacement of the fixing portion 46A in this embodiment.

The sensor 53 of the displacement detecting mechanism 52 detects the amount of displacement of the sensing wire 26 and the slave control circuit 13 receiving the output from the sensor 53 detects the opened and closed state of the pair of jaws 41. At this time, the opened and closed state of the pair of jaws 41 detected by the slave control circuit 13 is not affected by the difference between the degree of pulling of the driving wire 23 and the amount of movement of the fixing portion 46A which is caused by the stretching of the driving wire 23. That is, the opened and closed state of the pair of jaws 41 is detected with a high precision.

When the treatment tool 120 is used, the pair of jaws 41 may be opened and closed in a state where the bending part 28 is bent. In this case, the driving wire 23 and the sensing wire 26 both are bent at the bending axis 30. In this embodiment, in both the state where the bending part 28 bends and the state where the bending part 28 linearly extends, both the path length of the driving wire 23 and the path length of the sensing wire 26 in the bending part 28 are not changed. Accordingly, by detecting the amount of displacement of the sensing wire 26 without depending on the bending state of the bending part 28, it is possible to detect the opened and closed state of the pair of jaws 41 with a high precision.

As described above, according to the treatment tool 120, the slave arm 10 (manipulator), and the surgery support system 1 of this embodiment, the driving wire 23 is fixed to the fixing portion 46A of the connecting member 42A opening and closing the pair of jaws 41 and the sensing wire 26 is fixed to the sensing link 47 connected to the fixing portion 46A so as to move along with the fixing portion 46A. Accordingly, the operation of the pair of jaws 41 is precisely reflected in the displacement of the sensing wire 26 without being affected by the stretching of the driving wire 23. As a result, it is possible to detect the amount of displacement of the pair of jaws 41 provided in the treatment unit 40 with a high precision.

Fourth Embodiment

Figure 12:
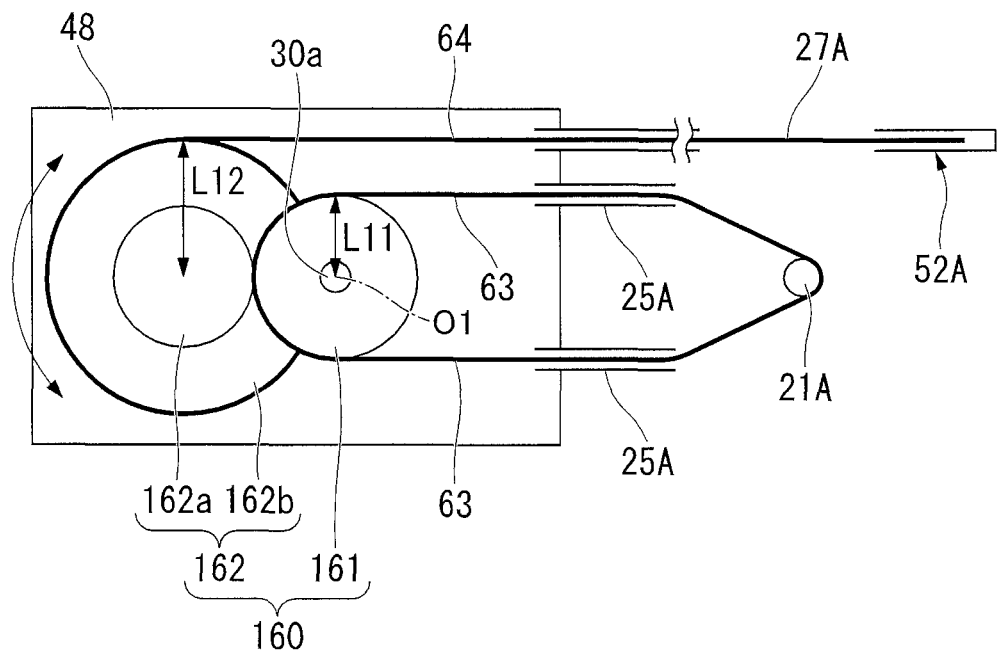
FIG. 12 is a diagram schematically illustrating a partial configuration of a treatment tool in a treatment tool, a manipulator, and a surgery support system according to a fourth embodiment of the invention.

A treatment tool, a manipulator, and a surgery support system according to a fourth embodiment of the invention will be described below. FIG. 12 is a diagram schematically illustrating a partial configuration of the treatment tool in the treatment tool, the manipulator, and the surgery support system according to this embodiment.

In this embodiment, a mechanism for bending the bending part 28 will be described in detail.

As shown in FIG. 12, the first bending axis 30a is a pulley group 160 composed of two pulleys (a first pulley 161 and a second pulley 162) having different diameters being connected to each other. The central axis line O1 of the first bending axis 30a is equal to the rotation center of the first pulley 161. The first pulley 161 is supported by the intermediate support member 29 so as to be rotatable about the rotation center of the first pulley 161 and is fixed to the support member 48. The bending wire 63 rotating the pulley group 160 is wound on the first pulley 161.

The large-diameter pulley (the second pulley 162) of the pulley group 160 includes a cylindrical engagement portion 162a frictionally engaging with the outer peripheral surface of the first pulley 161 and a disc-like body 162b coaxial with the engagement portion 162a. The bending detecting wire 64 of which an end is fixed to the body 162b is wound on the outer periphery of the body 162b. The second pulley 162 is rotatably connected to the support member 48. Accordingly, the second pulley 162 also rotates with the rotation of the first pulley 161.

In this embodiment, the distance (a second distance L12) from the rotation center (support point) of the second pulley 162 to the fixing position (the outer peripheral surface of the body 162b) of the bending detecting wire 64 is larger than the distance (a first distance L11) from the rotation center (support point) of the first pulley 161 to the fixing position (the outer peripheral surface of the first pulley 161) of the bending wire 63. The diameter of the first pulley 161 is larger than the diameter of the engagement portion 162a of the second pulley 162. Accordingly, when the first pulley 161 rotates, the rotation angle of the second pulley 162 is larger than the rotation angle of the first pulley 161. Accordingly, in this embodiment, the amount of displacement of the bending detecting wire 64 is larger than the amount of displacement of the bending wire 63.

The bending wire 63 is connected to a driving source 21A provided independently of the driving source 21 described in the first embodiment. In this embodiment, a servo motor or the like having a rotational output shaft on which the bending wire 63 is wound can be employed as the driving source 21A.

The bending detecting wire 64 is a wire of which the amount of displacement is detected by the displacement detecting mechanism 52A described in the second embodiment. In this embodiment, the amount of rotation of the pulley group 160 is detected by the slave control circuit 13 based on the amount of displacement detected by the displacement detecting mechanism 52A.

The bending wire 63 is inserted through the bending guide member 25A same as the driving guide member 25. The bending detecting wire 64 is inserted through the bending detecting guide member 27A same as the detecting guide member. The bending guide member 25A and the bending detecting guide member 27A are both fixed to the support member 48. The bending wire 63 extending from the bending guide member 25A to the first pulley 161 and the bending detecting wire 64 extending from the bending detecting guide member 27A to the body 162b of the second pulley 162 both extend substantially straight to the contact points with the pulleys along the tangential lines of the pulleys.

The operations of the treatment tool, the manipulator, and the surgery support system according to this embodiment will be described with focus on the operation of the bending part 28.

In this embodiment, the diameter of the second pulley 162 on which the bending detecting wire 64 is wound is larger than the diameter of the first pulley 161 on which the bending wire 63 is wound. The first pulley 161 and the second pulley 162 engage each other with the engagement portion 62a so that the rotation angle of the second pulley 162 is larger than the rotation angle of the first pulley 161. Accordingly, when the first pulley 161 is rotated by the bending wire 63, the amount of displacement of the bending detecting wire 64 is larger than the amount of displacement of the bending wire 63. That is, the pulley group 160 serves as an amplification mechanism amplifying the amount of movement of the bending detecting wire 64 with respect to the amount of movement of the bending wire 63. Similarly to the first embodiment, the amount of displacement of the bending detecting wire 64 is reflected in the degree of rotation of the second pulley 162 without being affected by the stretching of the bending wire 63 when a pulling force is applied to the bending wire 63.

The degree of rotation of the first pulley 161 represents the bending angle of the support member 48, to which the first pulley 161 is fixed, relative to the intermediate support member 29. The first pulley 161 and the second pulley 162 frictionally engage with each other. The second pulley 162 rotates by the degree of rotation reflecting the bending angle of the support member 48 relative to the intermediate support member 29. That is, in this embodiment, it is possible to detect the bending angle of the support member 48 relative to the intermediate support member 29 through the use of the bending detecting wire 64 with a high precision without being affected by the stretching of the bending wire 63 when a pulling force is applied to the bending wire 63.

In this embodiment, the amount of displacement of the bending detecting wire 64 can be larger than the amount of displacement of the bending wire 63 and it is thus possible to enhance a detection resolution in the displacement detecting mechanism 52A. By optimizing the ratio of the diameters of the pulleys constituting the pulley group 160 or the reduction ratio when transmitting the driving force from the first pulley 161 to the second pulley 162, a region in which the detectable range (dynamic range) of the displacement detecting mechanism 52A is wide can be used for the detection. As a result, it is hard to be affected from noise or the like, thus possible to enhance the detection precision.

A configuration employing the pulley group 160 can be applied to the second bending axis 30b, similarly to this embodiment.

A configuration employing the pulley group 160 can be applied to the opening and closing axis 41c, similarly to this embodiment.

Fifth Embodiment

Figure 13:
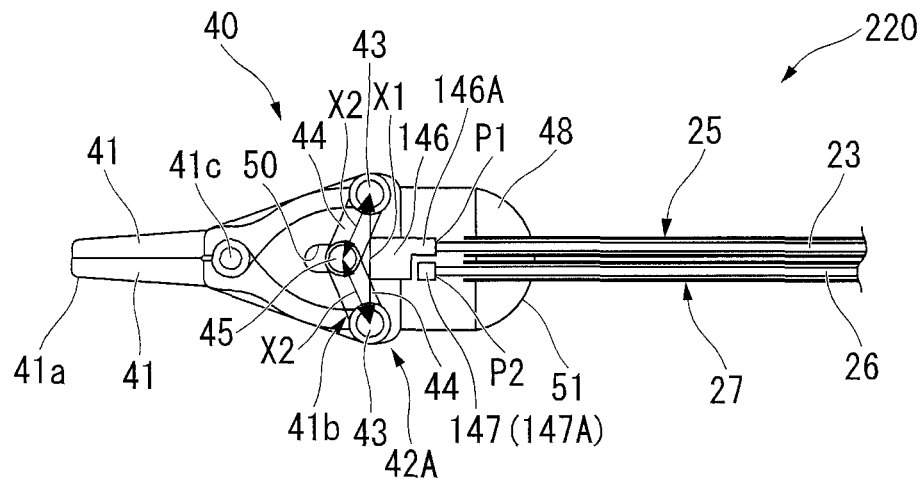
FIG. 13 is a diagram schematically illustrating a partial configuration configurational example of a treatment tool according to a fifth embodiment of the invention.

A treatment tool, a manipulator, and a surgery support system according to a fifth embodiment of the invention will be described below. FIG. 13 is a diagram schematically illustrating a partial configuration of the treatment tool according to this embodiment.

As shown in FIG. 13, in this embodiment, a treatment tool 220 has a configuration different from the treatment tool 120 described in the third embodiment.

In the treatment tool 220, the connecting portion 42A includes a fixing portion 146 and a sensing link 147. The fixing portion 146 has a permanent magnet 146A instead of the fixing portion 46A and the sensing link 47. The sensing link 147 has a permanent magnet 147A. The magnetic poles of the permanent magnet 146A formed in the fixing portion 146 and the permanent magnet 147A formed in the sensing link 147 are arranged to attract each other. The sensing wire 26 is fixed to the sensing link 147, similarly to the third embodiment.

In this embodiment, when the fixing portion 146 advances and retracts through the use of the driving wire 23, the permanent magnet 147A formed in the sensing link 147 is attracted by the magnetic force of the permanent magnet 146A formed in the fixing portion 146. Accordingly, the sensing link 147 moves in conjunction with the movement of the fixing portion 146. That is, in this embodiment, the fixing portion 146 and the sensing link 147 are connected to each other in a non-contact state by the magnetic force and the driving force from the driving source 21 is transmitted from the fixing portion 146 to the sensing link 147 through the use of the magnetic force. As a result, the sensing wire 26 fixed to the sensing link 147 moves along with the sensing link 147 and the amount of movement is detected by the displacement detecting mechanism 52, similarly to the third embodiment.

By employing this configuration, the same effects as in the third embodiment can be achieved. In this embodiment, the fixing portion 146 and the sensing link 147 can transmit the driving force in a non-contact state. Accordingly, when sterilizing the treatment tool 220, the gap through which liquid medicine or sterilizing gas can be infiltrated is large, thereby facilitating the sterilization.

Modified Example 5-1

Figure 14:
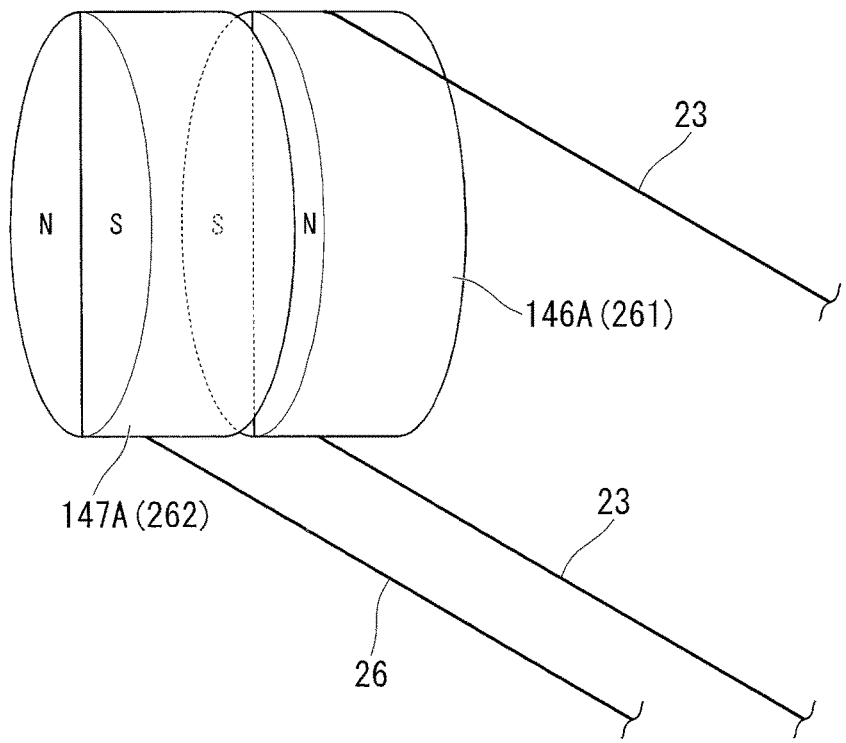
FIG. 14 is a diagram schematically illustrating a modified example of the fifth embodiment.

A modified example of the treatment tool 220 according to this embodiment will be described below. FIG. 14 is a diagram schematically illustrating the configuration of a modified example of the treatment tool according to this embodiment.

In this modified example, as shown in FIG. 14, the treatment unit 40 includes a first pulley 261 and a second pulley 262 instead of the fixing portion 146 and a sensing link 147. The first pulley 261 has a disc shape and has a permanent magnet 146A. The second pulley 262 has a disc shape and has a permanent magnet 147A. The first pulley 261 and the second pulley 262 are arranged so that the rotation centers thereof are coaxial, similarly to the first pulley 61 and the second pulley 62 described in the second embodiment. The first pulley 261 and the second pulley 262 have the same diameter.

In this modified example, the first pulley 261 and the second pulley 262 are not fixed to each other. The first pulley 261 and the second pulley 262 are connected to each other through the attracting magnetic force between the permanent magnet 146A and 147A so as to transmit the driving force generated from the driving source 21 and transmitted via the driving wire 23 from the first pulley 261 to the second pulley 262. In this modified example, the first pulley 261 and the second pulley 262 are connected to each other in a non-contact state through the magnetic force. By employing this configuration, the same effects as in the second embodiment can be achieved.

Figure 15:
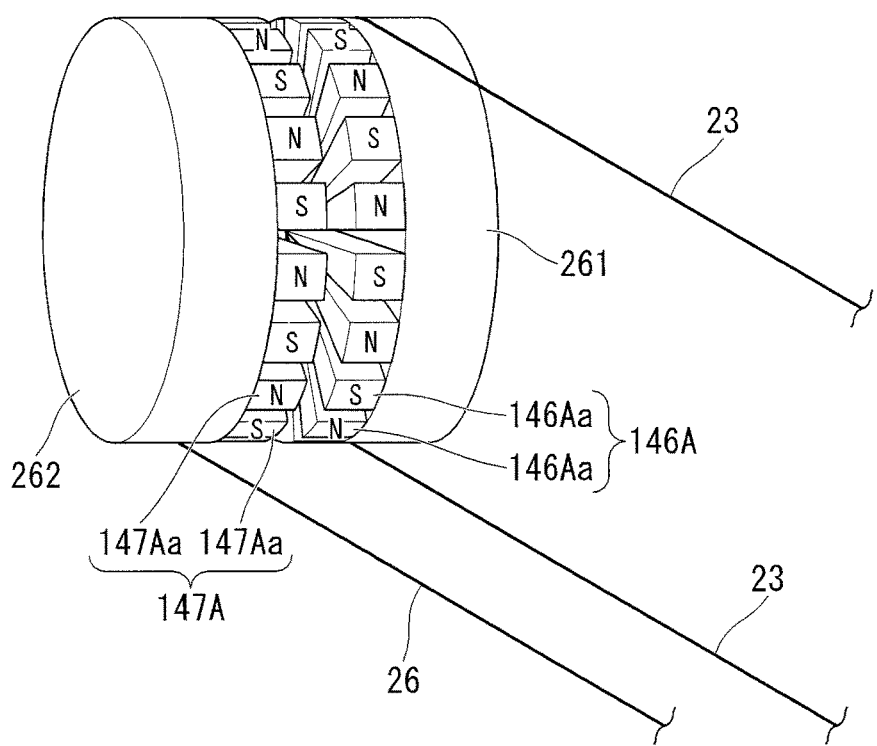
FIG. 15 is a diagram schematically illustrating another configuration of the modified example of the fifth embodiment.

The arrangement of the permanent magnet 146A in the first pulley 261 and the arrangement of the permanent magnet 147A in the second pulley 262 are not limited to the above-mentioned configuration. For example, as shown in FIG. 15, magnet pieces 146Aa may be arranged on the peripheral edge of the first pulley 261 and magnet pieces 147Aa may be arranged on the peripheral edge of the second pulley 262. In this case, the adjacent magnet pieces 146Aa on the first pulley 261 may be arranged so that the magnetic poles thereof are opposite to each other, and the adjacent magnet pieces 147Aa on the second pulley 262 may be arranged so that the magnetic poles are opposite to each other. Example of the magnetic poles are indicated by "N" and "S" in FIG. 15. By employing this configuration, it is possible to transmit the driving force through the use of the attractive force and the repulsive force between the magnet pieces 146Aa and the magnet pieces 147Aa.

Electromagnets may be employed instead of the permanent magnets 146A and 147A.

Electrostatic chucks attracting each other with an electrostatic force may be employed instead of transmitting the driving force through the use of the magnetic force of the permanent magnets 146A and 147A. In this case, the first pulley and the second pulley may be attracted to come in contact with each other when transmitting the driving force, or the first pulley and the second pulley may be in a non-contact state when transmitting the driving force.

Modified Example 5-2

Figure 16:
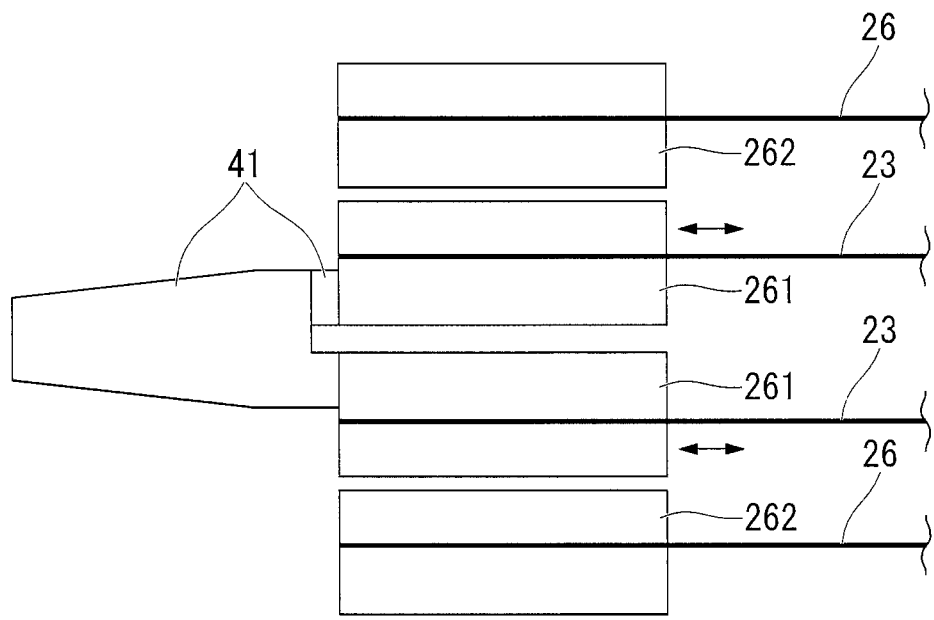
FIG. 16 is a diagram schematically illustrating another modified example of the fifth embodiment.

Another modified example of this embodiment will be described below. FIG. 16 is a diagram schematically illustrating the configuration in this modified example.

In this modified example, a set of the first pulley 261 and the second pulley 262 is formed for each of the pair of jaws 41. By employing this configuration, the jaws of the pair of jaws 41 can be made to move independently.

Sixth Embodiment

Figure 17:
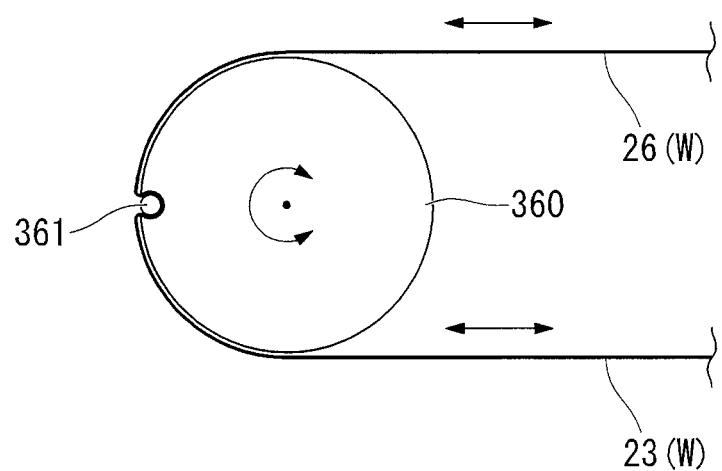
FIG. 17 is a diagram schematically illustrating a partial configuration of a treatment tool according to a sixth embodiment of the invention.

A treatment tool, a manipulator, and a surgery support system according to a sixth embodiment of the invention will be described below. FIG. 17 is a diagram schematically illustrating a partial configuration of the treatment tool according to this embodiment.

In this embodiment, the configuration in which a pulley 360 to which both the driving wire 23 and the sensing wire 26 are fixed is provided instead of the configuration of the second embodiment in which the first pulley 61 and the second pulley 62 are provided. The driving wire 23 and the sensing wire 26 do not have to be different wires, but a single wire may serve as the driving wire 23 and the sensing wire 26 as long as the intermediate portion of the single wire is fixed to the peripheral edge of the pulley 360. In this embodiment, a single wire W is fixed to a pin 361 in a state where the wire is wound on the pin 361 through the use of soldering or welding, and the wire W is fixed to the pulley 360 by inserting the pin 361 into the pulley 360. The method of fixing the wire W and the pulley 360 is not limited to the method using the pin 361. For example, the outer peripheral surface of the wire W may be fixed to the outer surface of the pulley 360 through the use of welding, soldering, or brazing.

In this embodiment, the pulley 260 is made to rotate by pulling and pushing the driving wire 23, and a pair of jaws 41 is opened and closed similarly to the second embodiment or the fourth embodiment. At this time, since the sensing wire 26 is fixed to the pulley 360, the sensing wire 26 moves along with the pulley 360. Since the sensing wire 26 is fixed to the pulley 360, the pulling force is not transmitted to the sensing wire 26 even when the driving wire 23 is pulled, as long as the sensing wire 26 is fixed to the pulley 360. In this embodiment, the same effects as in the above-mentioned embodiments can be achieved.

While preferred embodiments of the present invention have been described and illustrated above, it should be understood that these are exemplary of the present invention and are not to be considered as limiting. Additions, omissions, substitutions, and other modifications can be made without departing from the spirit or scope of the present invention.

Figure 18:
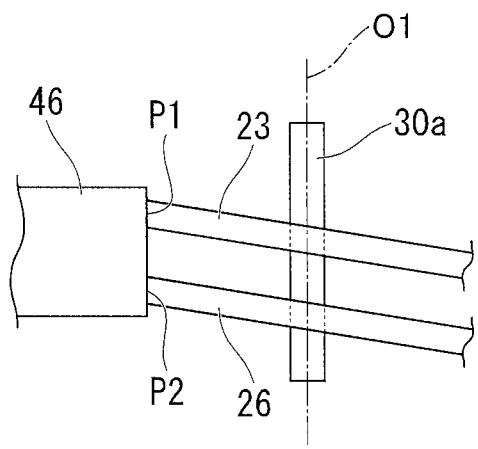
FIG. 18 is a diagram schematically illustrating another configurational example of the first embodiment of the invention.

For example, the first embodiment discloses an example where the driving wire 23 and the sensing wire 26 are drawn to be perpendicular to both the central axis line of the first bending axis 30a and the central axis line of the second bending axis 30b. However, when the first bending axis 30a or the second bending axis 30b is a cylindrical member extending in the direction perpendicular to the length direction (axis direction) of the intermediate support member 29, the driving wire 23 and the sensing wire 26 may be drawn to be substantially adjacent equally to each other at positions twisted about the central axis line O1 of the cylindrical member (the first bending axis 30a) along the outer periphery of the cylindrical member (the first bending axis 30a) (see FIG. 18). In this case, in the vicinity of the first bending axis 30a close to the fixing portion 46, it is possible to prevent the bending radii of the driving wire 23 and the sensing wire 26 from being different depending on the direction of flexion, and the influences on the wires 23 and 26 due to the bending of the bending part 28 can be prevented from being different depending on the direction of bending. When the wires 23 and 26 are arranged so that the projection planes of the wires 23 and 26 onto the cylindrical member are perpendicular to each other, it is particularly effective, which is preferable.

Figure 19:
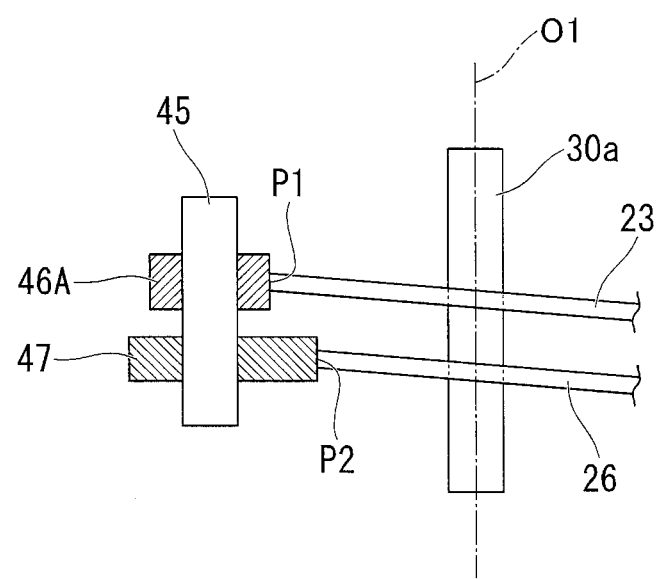
FIG. 19 is a diagram schematically illustrating another configurational example of the third embodiment of the invention.

The third embodiment discloses an example where the driving wire 23 and the sensing wire 26 are drawn to be perpendicular to both the central axis line of the first bending axis 30a and the central axis line of the second bending axis 30b. However, when the first bending axis 30a or the second bending axis 30b is a cylindrical member extending in the direction perpendicular to the length direction (axis direction) of the intermediate support member 29, the driving wire 23 and the sensing wire 26 may be drawn to be substantially adjacent equally to each other at positions twisted about the central axis line O1 of the cylindrical member (the first bending axis 30a) along the outer periphery of the cylindrical member (the first bending axis 30a) (see FIG. 19). In this case, in the vicinity of the first bending axis 30a close to the fixing portion 46A, it is possible to prevent the bending radii of the driving wire 23 and the sensing wire 26 from being different depending on the direction of bending, and the influences on the wires 23 and 26 due to the bending of the bending part 28 can be prevented from being different depending on the direction of bending. When the wires 23 and 26 are arranged so that the extending projection planes of the wires 23 and 26 onto the cylindrical member are perpendicular to each other, it is particularly effective, which is preferable.

The first embodiment discloses an example where the driving wire 23 is fixed directly to the fixing portion 46, but the driving wire 23 may be fixed indirectly to the fixing portion 46. For example, an intermediate member to which the fixing portion 46 and the driving wire 23 are both fixed may be provided. For example, a through-hole through which the driving wire 23 is inserted may be formed in the fixing portion 46 and an end of the driving wire 23 may be fixed to the fixing portion 46 in a state where the driving wire 23 is inserted through the through-hole.

The toggle mechanism is used as an example of the opening and closing mechanism in the first embodiment, but a so-called pantograph mechanism may be used.

The above-mentioned embodiments disclose the example where the links 44 and the fixing portion 46 are formed as a connecting member of the treatment unit for a pair of jaws 41 of the treatment unit, but the treatment unit and the connecting member may be integrated. In this case, for example, when one of the pair of jaws 41 is fixed and the other can be opened and closed, the proximal end of the other jaw 41 forms the connecting member to which the driving wire 23 and the sensing wire 26 are fixed, whereby the jaw and the connecting member are integrated.

The material of the driving wire and the sensing wire is not particularly limited. For example, a wire formed of metal such as stainless steel or tungsten or a wire formed of resin such as polyarylate may be employed. When the amount of displacement of a resin wire is detected by the use of a magnetic sensor, as long as the wire located in the vicinity of the magnetic sensor is covered with a metal small-diameter pipe, or is coated with metal, or is connected to a metal wire.

The above-mentioned embodiments discloses the example where a magnetic sensor is employed as a sensor detecting the displacement of the sensing wire, but the sensor detecting the displacement of the sensing wire is not limited to the magnetic type. For example, an optical sensor, an electrostatic capacitive sensor, a potentiometer, or the like may be employed as the sensor detecting the displacement of the sensing wire.

The example where the movement of the pair of jaws or the bending part formed in the treatment unit is detected is described in the above-mentioned embodiments and the modified examples thereof, but the configuration of the invention may be applied to detecting displacements of the joints of the slave arm.

The elements described in the above-mentioned embodiments and the modified examples thereof can be appropriately combined. Accordingly, the present invention is not to be considered as being limited by the foregoing description, and is only limited by the scope of the appended claims.

What is claimed is:

1. A surgery support system comprising:
a treatment tool comprising:
a shaft;
a wire extending through the shaft, the wire being configured to receive a driving force which generates a motion of the wire;
a treatment instrument disposed at a distal end of the shaft, wherein the treatment instrument comprises:
a connector configured to contact the wire, wherein the connector is configured to move in response to the motion of the wire; and
an elongated member having a distal end and a proximal free end,
wherein the elongated member extends through the shaft,
wherein a first portion of the elongated member is connected to the connector and is arranged closer to the distal end of the elongated member than the proximal free end of the elongated member,
wherein a second portion of the elongated member is arranged closer to the proximal free end of the elongated member than the distal end of the elongated member, and
wherein the elongated member is positioned relative to a sensor such that the second portion is arranged to move, due to movement of the connector in response to the motion of the wire, within a range of positions detectable by the sensor; and
a processor comprising hardware, wherein the processor is configured to:
receive an amount of movement of the elongated member sensed by the sensor based on detection by the sensor of movement of the second portion of the elongated member within the range of positions; and
control the treatment tool based on the amount of movement of the elongated member.

2. The surgery support system according to claim 1, further comprising:
an arm,
wherein the treatment tool is mounted on the arm.

3. The surgery support system according to claim 1, further comprising:
the sensor.

4. The surgery support system according to claim 1, further comprising:
a guide pipe extending through the shaft,
wherein the elongated member extends through the guide pipe.

5. The surgery support system according to claim 1, wherein the treatment instrument further comprises:
a pair of jaws configured to open and close in response to the movement of the connector.

6. The surgery support system according to claim 1, wherein the treatment instrument is configured to pivot about an axis with respect to the shaft in response to the movement of the connector.

7. The surgery support system according to claim 6, wherein the connector comprises:
a lever configured to pivot about the axis with respect to the shaft,
wherein the lever is configured to contact the wire, and
wherein the lever is connected to the first portion of the elongated member.

8. The surgery support system according to claim 6, wherein the connector comprises:
a first pulley, wherein the wire is wound on the first pulley; and
a second pulley, wherein the first portion of the elongated member is connected to the second pulley.

9. The surgery support system according to claim 8, wherein the first pulley and the second pulley are coaxially superimposed.

10. A treatment tool comprising:
a shaft;
a wire extending through the shaft, the wire being configured to receive a driving force which generates a motion of the wire;
a treatment instrument disposed at a distal end of the shaft, wherein the treatment instrument comprises:
a connector configured to contact the wire, wherein the connector is configured to move in response to the motion of the wire; and
an elongated member having a distal end and a proximal free end,
wherein the elongated member extends through the shaft,
wherein a first portion of the elongated member is connected to the connector and is arranged closer to the distal end of the elongated member than the proximal free end of the elongated member,
wherein a second portion of the elongated member is arranged closer to the proximal free end of the elongated member than the distal end of the elongated member, and
wherein the elongated member is positioned relative to a sensor such that the second portion is arranged to move, due to movement of the connector in response to the motion of the wire, within a range of positions detectable by the sensor,
wherein the treatment instrument is configured to pivot about an axis with respect to the shaft in response to the movement of the connector, and
wherein the connector comprises:
a lever configured to pivot about the axis with respect to the shaft,
wherein the lever is configured to contact the wire, and
wherein the lever is connected to the first portion of the elongated member.

* * * * *